United States Patent [19]

Butler et al.

[11] 4,451,580
[45] May 29, 1984

[54] METHOD OF PREPARING A SUPPORTED CATALYST

[75] Inventors: Graham Butler, Wantage; Christopher J. Wright, Abingdon, both of England

[73] Assignee: United Kingdom Atomic Energy Authority, London, England

[21] Appl. No.: 424,236

[22] Filed: Sep. 27, 1982

[30] Foreign Application Priority Data

Oct. 1, 1981 [GB] United Kingdom ................ 8129669

[51] Int. Cl.³ .................... B01J 21/04; B01J 23/46; B01J 23/74
[52] U.S. Cl. .................................... 502/335; 502/332; 502/337
[58] Field of Search ............... 502/332, 333, 334, 335, 502/336, 337, 338, 339

[56] References Cited

U.S. PATENT DOCUMENTS 4,124,629  11/1978  Hansford ..................... 252/466 J
4,273,680  6/1981  Halluin et al. ................ 252/466 J Primary Examiner—W. J. Shine
Attorney, Agent, or Firm—Larson and Taylor

[57] ABSTRACT

A supported catalyst is made by preparing a dispersion, contacting the dispersion with a substrate to produce a coating thereon, and firing and, if necessary, reducing to convert the dispersion to a catalytically active coating on the substrate. The catalyst may be useful in the catalysis of reactions for producing methane.

The dispersion is made by co-hydrolysis to give an intimate mixture of hydrolysis products (e.g. hydroxides of Ni and Al) convertible by calcining and, if necessary, reduction to produce the catalytically active coating in the form of one or more catalytically active components (e.g. Ni) and one or more ceramic oxides (e.g. $Al_2O_3$). Preferably, co-hydrolysis if effected by an agent such as urea which gives rise to no by-products in the coating.

11 Claims, No Drawings

METHOD OF PREPARING A SUPPORTED CATALYST

The invention relates to a method of preparing a supported catalyst comprising the steps of (i) preparing a dispersion; (ii) contacting the dispersion with a substrate to produce a coating thereon; and (iii) firing and, if necessary, reducing to convert the dispersion to a catalytically active coating on the substrate.

It is known in the art that chemical reactions that are either wholly or partially diffusion controlled and, or, have economics that are affected by pressure drop can be effected by passing reactant gases through single honeycombs which have been coated with aqueous dispersions of high surface area oxide supports such as $Al_2O_3$, $SiO_2$, $TiO_2$, $ZrO_2$ and $CeO_2$ and which have subsequently been dried and impregnated with a solution of a salt of a catalyst metal. See, for example, U.K. Pat. No. 1,492,929. It is also known that catalytic coatings for substrates can be made from dispersions made by dissolving soluble salts of catalytic metals in colloidal dispersions of oxide support material. See, for example, U.K. Pat. No. 1,568,861. The methods of manufacture are appropriate for producing catalytic coatings in which the catalytically active material (or component) is present in low concentration, and is dispersed over the whole surface of the oxide support. Examples of such catalysts include precious metal/alumina catalysts used for hydrocarbon oxidation. In many processes of industrial importance however, it may be desirable to use a catalyst in which catalytically active component(s) comprise a large proportion of its mass (e.g. greater than 10% by weight). Such processes include methanation, the low temperature shift reactions, methanol synthesis, and formula synthesis. In these processes, the catalysis can be nickel/alumina for the first process, copper/zinc oxide/alumina for the second and third processes and iron/molybdenum oxide for the fourth process.

The invention as claimed is intended to produce an adherent high surface area, catalytic coating in which catalytically active component(s) constitute a large proportion of the mass of the coating.

The invention includes a method of preparing a supported catalyst comprising the steps of
  (i) preparing a dispersion;
  (ii) contacting the dispersion with a substrate to produce a coating thereon; and
  (iii) firing and, if necessary, reducing, to convert the dispersion to a catalytically active coating on the substrate,
wherein the dispersion is prepared by co-hydrolysing a solution containing, as a first constituent, one or more compounds each having a hydrolysis product convertible to a catalytically active component under the conditions of step (iii) and containing, as a second constituent, one or more compounds each having a hydrolysis product convertible to a ceramic oxide under the conditions of step (iii), the co-hydrolysis being carried out under conditions such that an intimate mixture of the hydrolysis products is obtained in the dispersion; and step (iii) is carried out to convert the hydrolysis products to said catalytically active component(s) and to said ceramic oxide(s) thereby to produce a catalytically active coating on the substrate.

The above method may be carried out sequentially; the co-hydrolysis may, however, be carried out whilst the solution is in contact with the substrate.

By "dispersion" is meant a distribution of fine solid particles distributed substantially uniformly throughout a fluid, preferably water. It is important that the solid particles are not sufficiently large to make them difficult to maintain in dispersion or to give rise to a catalytically active coating of an unduly low surface area The role of the ceramic oxide (or oxides) may be to inhibit sintering of the active component(s). Also, the ceramic oxide(s) may itself participate in the catalytic process or processes in some way.

A supported catalyst made according to the invention may be used in a reactor to produce methane containing gases from mixtures of oxides of carbon and hydrogen according to the reaction schemes (1) and (2) below, usually termed "methanation", and to steam gasify hydrocarbons according to the reaction scheme (3) below. These reactions have great industrial importance. Steam gasification also includes processes in which hydrogen is added to the reactants, so that processes according to schemes (1) and (2) take place thereby giving rise to enhancement of the methane concentration in the product gases with respect to that of the carbon oxides.

$$CO + 3H_2 \rightarrow CH_4 + H_2O \qquad (1)$$

$$CO_2 + 4H_2 \rightarrow CH_4 + 2H_2O \qquad (2)$$

$$C_mH_n + H_2O \rightarrow XCH_4 + YCO + ZCO_2 \qquad (3)$$

Examples of compounds that may be used as the first constituents are those of MO, W, Cr, Mn, Re, Fe, Ru, Os, Co, Rh, Ir, Ni, Pd, Pt, Cu, Ag and Au. Ni is preferred because of its known value in the catalysis of methanation reactions, and its low current cost.

Examples of compounds that may be used as the second constituent are those which, following hydrolysis and firing, give $HfO_2$, $PbO$, $ZrO_2$, $CeO_2$, $TiO_2$, $Nb_2O_5$, $Ta_2O_5$, $SnO_2$, $In_2O_5$, $SiO_2$, $Al_2O_3$, $La_2O_3$, $ThO_2$, $U_3O_8$, $MgO$, $SrO$, $P_2O_5$ and $BaO$ and also includes cognate suboxides and higher oxides. Compounds of Al are preferred because of the known value of $Al_2O_3$ in the catalysis of methanation reactions.

By "co-hydrolysis" is meant that hydrolysis of the first constituent is effected during the same period of time as hydrolysis of the second constituent, though individual rates of and the moment of inception of hydrolysis may, of course, be different. Preferably, co-hydrolysis is effected by means of an agent which does not give rise to unwanted impurities in the coating. Such impurities are, in practice, difficult to remove before step (iii) is carried out and, if present in the supported catalyst, would deleteriously affect its performance. Examples of preferred co-hydrolysis agents are urea; hexamines; alkali metal carbonates and bicarbonates such as $Na_2CO_3$ and $NaHCO_3$; $(NH_4)_2CO_3$, $NH_4HCO_3$, water-soluble aliphatic amines, water-soluble aromatic amines, hydroxylamines and hydrazines or mixtures of such co-hydrolysis agents. Urea is particularly preferred.

The hydrolysis products will, in most cases, be hydroxides derived from the compounds present in the aqueous solution. Hydroxides includes, in this context, oxyhydroxides, hydrous or hydrated oxides, and complex structures containing hydroxyl ions.

Control of the co-hydrolysis conditions is required to ensure that an intimate mixture of the hydrolysis products is produced in the dispersion. This may be done, for example, by carrying out the co-hydrolysis under very mild conditions.

The dispersion produced has been found to be very stable and to possess appropriate rheological properties to enable it to be used in coating the substrate. In particular cases the coating has been found to possess thixotropic properties.

It is advisable for the dispersion to contain a high proportion of solid so that a coating of the desired thickness can be produced in a small number of stages, and so that there is minimal shrinking on drying, which can lead to the development of cracks within the coating. The concentration of the solid material as such in a dispersion of Ni and Al hydroxides may be between 10 and 1000 gms/liter although concentrations between 50 and 500 gms/liter are preferred. For dispersions containing other constituents, equivalent molar concentrations are preferred. In addition it is preferred that the individual particles in the dispersion are in the size range, 3 nm to 1000 nm. The dispersion may contain wetting agents and binders, grain growth inhibitors, ions which inhibit the rate at which $\gamma$-alumina is thermally converted to $\alpha$-alumina, stabilisers, promoters and materials which inhibit the deposition of carbon and the influence of prisons.

The dispersion may be used as such in step (ii) or it may be used in conjunction with other materials, for example to enhance resistance to sintering in the final catalyst or adhesion to the substrate. Examples of such other materials are inorganic oxide sols such as described in U.K. Patent Specifications Nos. 1,490,977 and 1,568,861. In addition other colloidal dispersions may be precoated onto the substrate to improve the properties of the catalyst such as lifetime and adhesion.

Step (ii) may be carried out by methods known in the art and is most conveniently carried out by immersing the substrate in the dispersion, removing and drying.

The substrate may be made of a ceramic material or of a metal. Examples of suitable ceramic materials are mullite, cordierite, silicon carbide, silicon nitride, zirconia and barium titanate. Examples of suitable metals are aluminum bearing iron base alloys, aluminium, stainless steels and high Ni content steels. An example of an aluminium bearing iron base alloy has a composition by weight of 10 to 30% Cr, 1 to 10% Al, 0 to 0.5% C and the balance iron. Other examples of such alloys may contain Y, for example 0.1 to 3.0% by weight. Such alloys are available in the U.K. under the U.K. Registered Trade Mark "FECRALLOY".

The substrate is preferably in a form such as to give a low pressure drop when reactants are passed through the final supported catalyst. Examples of such forms include tubes and honeycomb structures. Thus, the substrate may be a body fabricated, at least in part, of corrugated metal defining channels through the body, for example comprising spirally wound alternate plain and corrugated sheets wound in 'Swiss-roll' type fashion. Such a body may be held together by welding or by any suitable externally applied fastening means. A plurality of such bodies may, after being treated in accordance with the present invention, be arranged randomly in a container to constitute a catalyst device. See, for example, U.K. Patent Specification No. 2,077,136A. Advantages of the invention can be illustrated by contrasting the device with known methods of effecting methanation. In these methods reactant gases are typically passed through reactors containing a plurality of catalyst pellets which have been made by co-precipitating Ni and Al hydroxides and oxyhydroxides from aqueous solution followed by drying and forming. These pellets lead to a substantially greater pressure drop along a reactor than is experienced with a reactor containing catalysts made according to the invention.

In addition, it is believed that in the pelleted catalysts described above, the Al, in the form of $Al_2O_3$, contributes to the efficiency of the catalysts by virtue of being interposed between Ni grains thereby inhibiting sintering of the latter in use. This contrasts markedly with thermal sintering phenomena encountered in impregnated catalysts, whether those are impregnated pelleted catalysts, or impregnated coated catalysts. In the coating of the invention their crystal structures, as shown by their X-ray diffraction patterns, resemble closely the crystal structures of pellets produced by coprecipitation techniques.

Several ways of carrying out the invention will now be particularly described, by way of example only, as follows.

EXAMPLE 1

Preparation of Dispersion $[Ni(NO_3)_2]$ $(H_2O)_6$ (225 g) was dissolved in distilled water (360 ml). The resulting solution was stirred and $[Al(NO_3)_3]$ $(H_2O)_9$ (1135 g) added. The solution was then mixed into a solution of urea (375 g) in distilled water (2500 ml). The solids formed were dissolved and the mixture aged in air at 95° C. for 3-5 days. Alternatively the mixture may have been refluxed for 2-4 days in air. A green single phase gel was formed. There was no indication of any phase separation. The gel was redispersed to give a thixotropic colloidal dispersion by treating the gel with distilled water (250-600 ml) at pH 3.0-7.0 in a mechanical mixing device. The dispersion was observed to be stable for at least 12 months and was rendered fluid, when desired, by shaking or stirring. Thus, the dispersion exhibited typical non-Newtonian rheological properties. The dispersion contained 37.1 gms/liter of solid hydroxides.

The dispersion was dried in air to give a powdered catalyst and its catalytic activity for methanation measured after firing in air at 450° C. and reducing in hydrogen at 450° C. The activity was measured in a reactor where the inlet gas composition comprised 3 parts by volume of hydrogen and 1 part by volume of carbon monoxide.

The results are summarised in Table 1 below where comparison is made with a catalyst made by impregnating alumina with a solution of Ni ions. The yields are expressed as percentages of the total volume of the product gases passed through the chromatograph sampling loop.

|  | Space Velocity $hr^{-1}$ | Temperature at which 50% of Peak Activity was found | Methane Yield at | |
|---|---|---|---|---|
|  |  |  | 300° C. | 510° C. |
| Impregnated Nickel/Alumina (9% w/w) | 9,000 | 330° C. | 65% | 42% |
|  | 12,000 | 345° C. | 45% |  |
| Co-Hydrolysis 14.49% w/w | 9,000 | 295° C. | 72% | 45% |
|  | 120,000 | 275° C. | 30% | 20% |

$Na_2CO_3$ gave similar results when used as the co-hydrolysis agent.

Preparation of Supported Catalyst

Catalyst bodies of "FECRALLOY" (Registered Trade Mark) steel as described in U.K. Patent Specification No. 2,077,136A were pre-oxidised by heating in air and were then immersed in the dispersion prepared as described above, removed, air dried at 70° C. for 30 minutes, fired in air at 450° C. for 15 minutes and reduced in hydrogen at 450° C. for one hour. This gave a coating of Ni and $Al_2O_3$ on the bodies.

The bodies were then randomly packed in a tubular reactor and the catalytic activity for methanation of the resulting catalyst device tested using the same inlet gas composition as above. Methane yields were determined by gas chromatography.

TABLE II

| | Space* Velocity | Light off Temperature | Yield 510° C. |
|---|---|---|---|
| Co-Hydrolysis 5% of the weight of the device was catalyst film | 9,400 $hr^{-1}$ | 275° C. | 43% |

*Calculated by assuming that the volume of the catalyst is equivalent to the sum of the enclosed volumes of each individual monolith.

EXAMPLE 2

Preparation of Dispersion $[Ni(NO_3)_2]$ $(H_2O)_6$ (530.1 g) was dissolved in distilled water (Total volume 1500 ml). The resulting solution was stirred and $[Al(NO_3)_3]$ $(H_2O)_9$ (284.8 g) was added and the volume of the solution made up to 2625 ml with further distilled water. The first solution was then added dropwise to a solution of $Na_2CO_3$ $10H_2O$ (1500 g) in water (5500 ml) over a period of 1.5 hrs. The solids produced were washed repeatedly in distilled water by slurrying and decanting.

The slurry was then aged at 60° C. to produce a thixotropic gel which could be used imediately as a coating fluid, or, if required, after dilution.

Prepation of Catalyst Bodies

Nine catalyst bodies of "Fecralloy" steel as described in U.K. Patent Specification No. 2,077,136A were preoxidised by heating in air, and then immersed in the dispersion prepared as described above, removed, air dried at 70° C. for 30 minutes, fired in air at 450° C. for 15 minutes and reduced in hydrogen at 450° C. for one hour. The total mass of catalyst coated onto the artefacts, amounted to 4.31% of the final mass of the catalyst (The nickel content of the coating was 49.6%). The catalyst bodies were randomly packed in a tubular reactor together with small pieces of silica chip. The catalytic activity for methanation was testing using the same inlet gas composition as Example 1. Methane yields were determined taking samples of the cooled product gases and analysing them by gas chromatography.

The initial yield of methane was 66% of the product gases.

Without disturbing the contents of the reactor, they were then subjected to an accelerated aging test, in which a mixture of $H_2O$ vapour and hydrogen in the volume ratio of 9:1 was passed through the reactor at 700° C.

After aging the activity was measured. After 17.7 hours the maximum methane yield was 53%, and after 86.4 hours the maximum yield was 35%. These conversions are very useful in view of the small amounts of active phase present in the reactor.

EXAMPLE 3

Preparation of Dispersion

Commercial "$Ru(NO)(NO_3)_3$" solution (1.93$^w$/oRu; 62 ml) was mixed with a solution of $[Al(NO_3)_3](H_2O)_9$ (219 g) dissolved in distilled water (1100 ml). This solution was then added dropwise with stirring to a solution of $Na_2CO_3.10H_2O$ (529 g) dissolved in distilled water (2000 ml). The mixture was then added at 80° C. over a period of 36 hours. The resultant gel was then mixed with distilled water (150 ml) to yield a dispersion of hydrous oxides that was stable for at least 2 weeks.

The dispersion prepared above was used to coat a substrate as described in Examples 1 and 2.

We claim:

1. A method of preparing a supported catalyst comprising the steps of:
   (i) providing an aqueous hydrolysis solution containing, as a first constituent, one or more compounds each being hydrolysable to a hydroxide convertible to a catalytically active component under the conditions of step (v) below, and containing, as a second constituent, one or more compounds each being hydrolysable to a hydroxide convertible to a ceramic oxide under the conditions of step (v) below;
   (ii) providing said aqueous hydrolysis solution in an aqueous hydrolysis agent solution comprising a co-hydrolysis agent to effect hydrolysis of said first and second hydrolysable constituents under conditions such that an aqueous dispersion comprising an intimate mixture of said hydroxides is produced;
   (iii) converting the aqueous dispersion to a thixotropic dispersion by a process including aging the aqueous dispersion by subjecting it to a heat treatment to give a gel;
   (iv) contacting the thixotropic dispersion with a substrate to produce a coating thereon; and
   (v) firing to convert said hydroxides to said catalytically active component and to said ceramic oxide thereby to produce a catalytically active coating on the substrate.

2. A method as claimed in claim 1 wherein the first constituent comprises a nickel compound and the catalytically active component comprises nickel.

3. A method as claimed in claim 1 and wherein the catalytically active component comprises nickel and the ceramic oxide comprises alumina wherein the total solid concentration in the dispersion is in the range of 10 to 1000 gram per liter.

4. A method as claimed in claim 3 wherein the total solid concentration in the dispersion is in the range of 50 to 500 gram per liter.

5. A method as claimed in claim 1 wherein step (ii) comprises adding said aqueous hydrolysis solution to said aqueous hydrolysis agent solution.

6. A method as claimed in claim 5 wherein step (iii) comprises aging the aqueous dispersion formed in step (ii) to form a gel and re-dispersing said gel to form said thixotropic dispersion.

7. A method according to claim 6 wherein step (iv) comprises immersing said substrate into said thixotropic dispersion, removing the immersed substrate from the dispersion, and drying the removal substrate.

8. A method according to claim 7 wherein said substrate comprises a structure having a form so as to give a low pressure drop when reactants are passed through the supported catalyst.

9. A method according to claim 8 wherein said structure comprises a tube or honeycomb.

10. A method according to claim 9 wherein said structure is fabricated of metal.

11. A method according to claim 8 wherein said structure comprises a body fabricated, at least in part, of corrugated metal defining channels through the body.

* * * * *